United States Patent

Ogawa et al.

[11] Patent Number: 5,232,701
[45] Date of Patent: Aug. 3, 1993

[54] BORON CARBONATE AND SOLID ACID PESTICIDAL COMPOSITION

[75] Inventors: Masao Ogawa, Toyonaka; Toshiro Ohtsubo, Sanda; Shigenori Tsuda, Kyoto, all of Japan

[73] Assignee: Sumitomo Chemical Company, Limited, Osaka, Japan

[21] Appl. No.: 774,342

[22] Filed: Oct. 10, 1991

[30] Foreign Application Priority Data

Oct. 11, 1990 [JP] Japan .................................. 2-274984
Jan. 22, 1991 [JP] Japan .................................. 3-022899

[51] Int. Cl.$^5$ ...................... A01N 25/12; A01N 55/08
[52] U.S. Cl. .................................. 424/408; 424/409; 424/466; 424/489; 504/116
[58] Field of Search ............... 424/405, 466, 470, 489; 71/128, 3

[56] References Cited

U.S. PATENT DOCUMENTS

| | | | |
|---|---|---|---|
| 2,773,757 | 5/1953 | Connell et al. | 71/128 |
| 3,531,278 | 9/1970 | Nies | 71/128 |
| 4,034,038 | 7/1977 | Vogel | 260/462 R |
| 4,933,000 | 6/1990 | Somlo | 71/93 |
| 5,055,305 | 10/1991 | Young | 424/466 |

FOREIGN PATENT DOCUMENTS

| | | |
|---|---|---|
| 3017639 | 11/1981 | Fed. Rep. of Germany . |
| 2579464 | 10/1986 | France . |
| 45-24360 | 8/1970 | Japan . |
| 47-27930 | 7/1972 | Japan . |
| 50-20128 | 7/1975 | Japan . |
| 51-88641 | 8/1976 | Japan . |
| 55-2402 | 1/1980 | Japan . |
| 59-030879 | 2/1984 | Japan . |
| 62-164601 | 7/1987 | Japan . |
| 2139893 | 11/1984 | United Kingdom . |
| 2184946 | 7/1987 | United Kingdom . |
| 9000007 | 1/1990 | World Int. Prop. O. . |

OTHER PUBLICATIONS

Chemical Abstracts, vol. 100, No. 26, Jun. 25, 1984, Columbus, Ohio, US; abstract No. 215536Y, 'Stable effervescent tablets' p. 345; & JP-A-59 030879 (Nissan Chemical Industries Ltd). Feb. 18, 1984.

Primary Examiner—Thurman K. Page
Assistant Examiner—Neil Levy
Attorney, Agent, or Firm—Stevens, Davis, Miller & Mosher

[57] ABSTRACT

A composition excellent in dispersibility and diffusion in water, and storage stability comprising a) a pesticidal active ingredient, b) a surface active agent, c) a carbonate, d) a solid acid and e) at least one selected from the group consisting of boron oxide and metaboric acid, wherein at least one of the carbonate and the solid acid is water-soluble, the total content of the carbonate and the solid acid is in a proportion of 5–90% to the total weight, the weight ratio of the carbonate to the solid acid is in the range of 1:10–10:1, and the weight of at least one selected from the group consisting of boron oxide and metaboric acid is in a proportion of 0.5–40% to the total weight.

10 Claims, 1 Drawing Sheet

BORON CARBONATE AND SOLID ACID PESTICIDAL COMPOSITION

The present invention relates to fizzy granules and fizzy tablets containing pesticide.

Figure 1:
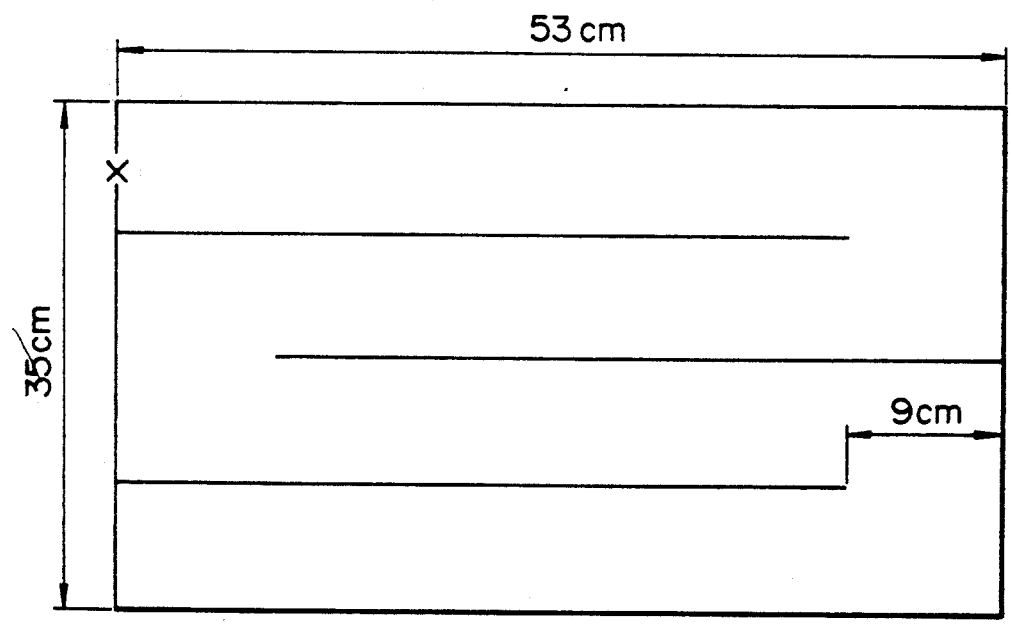
FIG. 1 shows a VAT used in test example 2

As the fizzy granules and fizzy tablets containing pesticide, there have hitherto been known those described in Japanese Examined Patent Publication Nos. 24360/1970, 27930/1972 and 20128/75.

These formulations had problems such as poor stability during storage.

That is, both carbonates and solid acids are present in the conventional formulations, which are observed to generate carbon dioxide gas due to the absorption of moisture in air during their storage in a container such as a kraft bag, a polyethylene bag or a polyethylene bottle and thus cause the problem of decreasing the weight of the product. These formulations also have problems such as the deterioration of disintegrability in water, dispersibility in water or diffusion ability in water upon storage for a long period. Furthermore, when these preparations are stored in a polyethylene-laminated aluminium bag having no gas permeability, the bag is often expanded by the generated carbon dioxide gas.

There is the danger of breaking the bag at the violent reaction.

In consideration of the states, the present inventors have found a fizzy granules and fizzy tablets comprising a pesticidal active ingredient, a surface active agent, a carbonate, a solid acid and at least one selected from boron oxide and metaboric acid and having an excellent storage stability.

The present invention relates to a pesticidal formulation (referred to hereinafter as the composition of the present invention) comprising a) a pesticidal active ingredient, b) a surface active agent, c) a carbonate, d) a solid acid and e) at least one selected from boron oxide ($B_2O_3$) and metaboric acid, wherein at least one of the carbonate and the solid acid is water-soluble, the total content of the carbonate and the solid acid is in a proportion of 5–90% to the total weight, the weight ratio of the carbonate to the solid acid is in the range of 1:10–10:1, and the weight of the boron oxide and/or metaboric acid is in a proportion of 0.5–40%, preferably 1–15% to the total weight.

In the composition of the present invention, the pesticidal active ingredient used is not limited specifically and includes the following compounds, active isomers thereof or mixtures thereof.

Typical compounds are listed together with the compound numbers in the following:

(1) α-cyano-3-phenoxybenzyl 2-(4-chlorophenyl)-3-methylbutyrate,
(2) (S)-α-cyano-3-phenoxybenzyl (S)-2-(4-chlorophenyl)-3-methylbutyrate,
(3) α-cyano-3-phenoxybenzyl 2,2,3,3-tetramethylcyclopropanecarboxylate,
(4) 3-phenoxybenzyl 3-(2,2-dichlorovinyl)-2,2-dimethylcyclopropanecarboxylate,
(5) 3-phenoxybenzyl chrysanthemate,
(6) 3-phenoxybenzyl (1R)-chrysanthemate,
(7) α-cyano-3-phenoxybenzyl 3-(2,2-dichlorovinyl)-2,2-dimethylcyclopropanecarboxylate,
(8) α-cyano-3-(4-bromophenoxy)benzyl 3-(2,2-dichlorovinyl)-2,2-dimethylcyclopropanecarboxylate,
(9) α-cyano-3-(4-fluorophenoxy)benzyl 3-(2,2-dichlorovinyl)-2,2-dimethylcyclopropanecarboxylate,
(10) α-cyano-3-(3-bromophenoxy)benzyl 3-(2,2-dichlorovinyl)-2,2-dimethylcyclopropanecarboxylate,
(11) α-cyano-3-(4-chlorophenoxy)benzyl 3-(2,2-dichlorovinyl)-2,2-dimethylcyclopropanecarboxylate,
(12) α-cyano-3-phenoxybenzyl chrysanthemate,
(13) α-cyano-3-phenoxybenzyl (1R)-chrysanthemate,
(14) α-cyano-3-(4-bromophenoxy)benzyl 2-(4-chlorophenyl)-3-methylbutyrate,
(15) α-cyano-3-(3-bromophenoxy)benzyl 2-(4-chlorophenyl)-3-methylbutyrate,
(16) α-cyano-3-(4-chlorophenoxy)benzyl 2-(4-chlorophenyl)-3-methylbutyrate,
(17) α-cyano-3-(4-fluorophenoxy)benzyl 2-(4-chlorophenyl)-3-methylbutyrate,
(18) α-cyano-3-phenoxybenzyl 2-(4-bromophenyl)-3-methylbutyrate,
(19) α-cyano-3-phenoxybenzyl 2-(4-tert-butylphenyl)-3-methylbutyrate,
(20) α-cyano-3-phenoxybenzyl 2-(3,4-methylenedioxyphenyl)-3-methylbutyrate,
(21) α-cyano-4-fluoro-3-phenoxybenzyl 3-(2,2-dichlorovinyl)-2,2-dimethylcyclopropanecarboxylate,
(22) α-cyano-3-phenoxybenzyl 2-(2-chloro-4-trifluoromethylanilino)-3-methylbutyrate,
(23) α-cyano-3-phenoxybenzyl 2-(4-difluoromethoxyphenyl)-3-methylbutyrate,
(24) α-cyano-3-phenoxybenzyl (S)-2-(4-difluoromethoxyphenyl)-3-methylbutyrate,
(25) α-cyano-(5-phenoxy-2-pyridyl)methyl 3-(2,2-dichlorovinyl)-2,2-dimethylcyclopropanecarboxylate,
(26) α-cyano-3-phenoxybenzyl 2,2-dimethyl-3-(1,2,2,2-tetrabromoethyl)cyclopropanecarboxylate,
(27) α-cyano-3-phenoxybenzyl 2,2-dimethyl-3-(1,2-dichloro-2,2-dibromoethyl)cyclopropanecarboxylate,
(28) α-cyano-3-phenoxybenzyl 1-(4-ethoxyphenyl)-2,2-dichlorocyclopropanecarboxylate,
(29) α-cyano-3-phenoxybenzyl 2,2-dimethyl-3-(2-chloro-2-trifluoromethylvinyl)cyclopropanecarboxylate,
(30) 2-(4-ethoxyphenyl)-2-methylpropyl 3-phenoxybenzyl ether,
(31) 2-(4-ethoxyphenyl)-3,3,3-trifluoropropyl 3-phenoxybenzyl ether,
(32) 2-methyl-3-phenylbenzyl (1R, trans)-2,2-dimethyl-3-(2-chloro-2-trifluoromethylvinyl)cyclopropanecarboxylate,
(33) 2,3,5,6-tetrafluoro-4-methylbenzyl (1R, trans)-2,2-dimethyl-3-(2-chloro-2-trifluoromethylvinyl)cyclopropanecarboxylate,
(34) 3,4,5,6-tetrahydrophthalimidomethyl chrysanthemate,
(35) 3,4,5,6-tetrahydrophthalimidomethyl (1R)-chrysanthemate,
(36) 3-allyl-2-methyl-4-oxocyclopent=2-enyl chrysanthemate,
(37) 3-allyl-2-methyl-4-oxocyclopent-2-enyl (1R)-chrysanthemate,

(38) (S)-2-methyl-4-oxo-3-(2-propynyl)cyclopent-2-enyl (1R)-chrysanthemate,
(39) 1-ethynyl-2-methyl-2-pentenyl (1R)-chrysanthemate,
(40) 5-benzyl-3-furylmethyl chrysanthemate,
(41) 5-benzyl-3-furylmethyl (1R)-chrysanthemate,
(42) α-cyano-3-(4-bromophenoxy)benzyl 3-(2,2-dibromovinyl)-2,2-dimethylcyclopropanecarboxylate,
(43) O,O-dimethyl O-(3-methyl-4-nitrophenyl) phosphorothioate,
(44) O,O-dimethyl S-[1,2-di(ethoxycarbonyl)ethyl] phosphorodithioate,
(45) O,O-dimethyl O-(4-cyclophenyl) phosphorothioate,
(46) O,O-dimethyl S-(α-ethoxycarbonylbenzyl) phosphorodithioate,
(47) O,O-diethyl O-(2-isopropyl-4-methyl-6-pyrimidinyl) phosphorothioate,
(48) O,O-dimethyl O-[3-methyl-4-(methylthio)phenyl] phosphorothioate,
(49) O-(4-bromo-2,5-dichlorophenyl) O,O-diethylphosphorothioate,
(50) 2-methoxy-4H-1,3,2-benzoxaphosphorin-2-sulfide,
(51) O,O-dimethyl O-(2,4,5-trichlorophenyl) phosphorothioate,
(52) O,O-diethyl O-(3,5,6-trichloro-2-pyridyl) phosphorothioate,
(53) O,O-dimethyl O-(3,5,6-trichloro-2-pyridyl) phosphorothioate,
(54) O,O-dimethyl O-(4-bromo-2,5-dichlorophenyl) phosphorothioate,
(55) dimethyl 2,2-dichlorovinylphosphate,
(56) O,S-dimethyl N-acetylphosphoroamidothioate,
(57) O-(2,4-dichlorophenyl) O-ethyl S-propyl phosphorodithioate,
(58) O,O-dimethyl S-(5-methoxy-1,3,4-thiadiazolin-2-on-3-ylmethyl) phosphorodithioate,
(59) dimethyl 2,2,2-trichloro-1-hydroxyethylphosphonate,
(60) O-ethyl O-(4-nitrophenyl) benzenephosphonothioate,
(61) O,O-dimethyl S-(N-methylcarbamoylmethyl) phosphorodithioate,
(62) 2-sec-butylphenyl N-methylcarbamate,
(63) 3-methylphenyl N-methylcarbamate,
(64) 3,4-dimethylphenyl N-methylcarbamate,
(65) 2-isopropoxyphenyl N-methylcarbamate,
(66) 1-naphthyl N-methylcarbamate,
(67) 2-isopropylphenyl N-methylcarbamate,
(68) O,O-diethyl S-[2-(ethylthio)ethyl]phosphorodithioate,
(69) S-methyl N-[(methylcarbamoyl)oxy]thioacetoimidate,
(70) trans-5-(4-chlorophenyl)-N-cyclohexyl-4-methyl-2-oxothiazolidin-3-carboxamide,
(71) 2,3-dihydro-2,2-dimethyl-7-benzofuranyl N-dibutylaminothio-N-methylcarbamate,
(72) N,N-dimethyl-1,2,3-trithian-5-ylamine,
(73) 1,3-bis(carbamoylthio)-2-(N,N-dimethylamino)-propane hydrochloride,
(74) ethyl N-[2,3-dihydro-2,2-dimethylbenzofuran-7-yloxycarbonyl(methyl)aminothio]-N-isopropyl-β-alaninate,
(75) 1-[3,5-dichloro-4-(3-chloro-5-trifluoromethyl-2-pyridyloxy)phenyl]-3-(2,6-difluorobenzoyl)urea,
(76) 1-(3,5-dichloro-2,4-difluorophenyl)-3-(2,6-difluorobenzoyl)urea,
(77) 1-[3,5-dichloro-4-(1,1,2,2-tetrafluoroethoxy)-phenyl]-3-(2,6-difluorobenzoyl)urea,
(78) ethyl 2-(4-phenoxyphenoxy)ethylcarbamate,
(79) 2-tert-butyl-5-(4-tert-butylbenzylthio)-4-chloropyridazin-3(2H)-one,
(80) 1-[4-(2-chlor-4-trifluoromethylphenoxy)-2-fluorophenyl]-3-(2,6-difluorobenzyl)urea,
(81) tert-butyl (E)-α-(1,3-dimethyl-5-phenoxypyrazol-4-ylmethyleneaminoxy)-p-toluate,
(82) 3,7,9,13-tetramethyl-5,11-dioxa-2,8,14-trithia-4,7,9,13-tetraazapentadeca-3,12-diene-6,10-dione,
(83) 1-(6-chloro-3-pyridylmethyl)-N-nitroimidazolidin-2-ylidenamine,
(84) 5-ethoxy-3-trichloromethyl-1,2,4-triadiazole,
(85) O,O-diisopropyl S-benzyl phosphorothiolate,
(86) O-ethyl S,S-diphenyl dithiophosphate,
(87) Polyoxin,
(88) Blastocidine S,
(89) 3,4-dichloropropionanilide,
(90) isopropyl N-(3-chlorophenyl)carbamate,
(91) S-ethyl N,N-dipropylthiolcarbamate,
(92) 3-methoxycarbonylaminophenyl N-(3-methylphenyl)carbamate,
(93) N-methoxymethyl-2-chloro-2',6'-diethylacetanilide,
(94) 2,6-dinitro-N,N-dipropyl-4-trifluoromethylaniline,
(95) S-(4-chlorobenzyl) N,N-diethylthiolcarbamate,
(96) S-ethyl N,N-hexamethylenethiolcarbamate,
(97) N-(1,1,3-trimetyl-2-oxa-4-indanyl)-5-chloro-1,3-dimethylpyrazol-4-carboxyamide,
(98) 3'-isopropoxy-2-(trifluoromethyl)benzanilide,
(99) diisopropyl 1,3-dithiolan-2-ilidenemalonate,
(100) 1,2,5,6-tetrahydropyrrolo[3,2,1-i,j]quinolin-4-one,
(101) 3-allyloxy-1,2-benzoisothiazole-1,1-dioxide,
(102) 5-methyl[1,2,4]triazolo[3,4-b]benzothiazole,
(103) 1,2-bis(3-methoxycarbonyl-2-thioureido)benzene,
(104) 1-(4-chlorobenzyl)-1-cyclopentyl-3-phenylurea,
(105) Validamycin A
(106) 6-(3,5-dichloro-4-methylphenyl)-3(2H)-pyridazinone,
(107) Kasugamycin hydrochloride,
(108) Methyl 1-(butylcarbamoyl)benzimidazole-3-carbamate,
(109) 3-(3,5-dichlorophenyl)-N-isopropyl-2,4-dioxoimidazolidine-1-carboxamide,
(110) 3-(3,5-dichlorophenyl)-5-methyl-5-vinyl-1,3-oxazolidine-2,4-dione,
(111) manganese ethylenebisdithiocarbamate,
(112) manganese and zinc ethylenebisdithiocarbamate,
(113) N-(trichloromethylthio)cyclohex-4-en-1,2-dicarboximide,
(114) 3'-isopropoxy-2-methylbenzanilide,
(115) 3-hydroxy-5-methylisoxazole,
(116) tetrachloroisophthalonitrile,
(117) 1,1'-iminodi(octamethylene)diguanidine,
(118) 1-(4-chlorophenoxy)-3,3-dimethyl-1-(1H-1,2,4-triazol-1-yl)butanone,
(119) (E)-4-chloro-2-(trifluoromethyl)-N-[1-(imidazol-1-yl)-2-propoxyethylidene]aniline,
(120) methyl N-(methoxyacetyl)-N-(2,6-dimethylphenyl)-alaninate,
(121) 3-chloro-N-(3-chloro-5-trifluoromethyl-2-pyridyl)-2,6-dinitro-4-methylaniline,
(122) N-butoxymethyl-2-chloro-2',6'-diethylacetanilide,
(123) O-ethyl O-(5-methyl-2-nitrophenyl)-sec-butyl phosphoroamidethioate,
(124) ethyl N-chloroacetyl-N-(2,6-diethylphenyl)-glycinate, (125) 2-[1-methyl-2-(4-phenoxyphenoxy)ethoxy]pyridine,
(126) (E)-1-(4-chlorophenyl)-4,4-dimethyl-2-(1H-1,2,4-triazol-1-yl)-1-penten-3-ol,
(127) 1-(4-chlorophenyl)-4,4-dimethyl-2-(1H-1,2,4(triazol-1-yl)-1-pentan-3-ol,
(128) 2-bromo-N-(α,α-dimethylbenzyl)-3,3-dimethylbutanamide,
(129) 1-(1-methyl-1-phenylethyl)-3-(p-tolyl)urea,
(130) 2-(2-naphthoxy)propionanilide,
(131) 2-(2,4-dichloro-3-methylphenoxy)propionanilide,
(132) 4-(2,4-dichlorobenzoyl)-1,3-dimethyl-5-pyrazolyl p-toluenesulfonate,
(133) 4-(2,4-dichlorobenzoyl)-1,3-dimethyl-5-phenacyloxypyrazole,
(134) 4-(2,4-dichloro-3-methylbenzoyl)-1,3-dimethyl-5-(4-methylphenacyloxy)pyrazole,
(135) 2,4,6-trichlorophenyl 4-nitrophenyl ether,
(136) 2,4-dichlorophenyl 3-methoxy-4-nitrophenyl ether,
(137) 2,4-dichlorophenyl 3-methoxycarbonyl-4-nitrophenyl ether,
(138) 2-benzothiazol-2-yloxy-N-methylacetanilide,
(139) 2',3'-dichloro-4-ethoxymethoxybenzanilide,
(140) 5-tert-butyl-3-(2,4-dichloro-5-isopropoxyphenyl)-1,3,4-oxadiazol-2(3H)-one,
(141) 2-amino-3-chloro-1,4-naphthoquinone,
(142) methyl 2-[3-(4,6-dimethoxypyrimidin-2-yl)-ureidosulfonylmethyl]benzoate,
(143) 3,7-dichloroquinoline-8-carboxylic acid,
(144) ethyl 5-[3-(4,6-dimethoxypyrimidin-2-yl)ureidosulfonyl]-1-methylpyrazole-4-carboxylate,
(145) 3-chloro-2-[4-chloro-2-fluoro-5-(2-propionyloxy)-phenyl]-4,5,6,7-tetrahydro-2H-indazole,
(146) O-(4-tert-butylphenyl) N-(6-methoxy-2-pyridyl)-N-methylthionocarbamate,
(147) O-(3-tert-butylphenyl) N-(6-methoxy-2-pyridyl)-N-methylthionocarbamate,
(148) O-(4-chloro-3-ethylphenyl) N-(6-methoxy-2-pyridyl)-N-methylthionocarbamate,
(149) O-(4-bromo-3-ethylphenyl) N-(6-methoxy-2-pyridyl)-N-methylthionocarbamate,
(150) O-(3-tert-bytyl-4-chlorophenyl) N-(6-methoxy-2-pyridyl)-N-methylthionocarbamate,
(151) O-(4-trifluoromethylphenyl) N-(6-methoxy-2-pyridyl)-N-methylthionocarbamate,
(152) 1-(2-chlorobenzyl)-3-(α,α-dimethylbenzyl)-urea,
(153) N-(3,5-dichlorophenyl)-1,2-dimethylcyclopropane-1,2-dicarboximide,
(154) O-(2,6-dichloro-4-methoxyphenyl) O,O-dimethyl phosphorothioate,
(155) 1-ethyl-1,4-dihydro-6,7-methylenedioxy-4-oxo-3-quinolinecarboxylic acid,
(156) (E)-1-(2,4-dichlorophenyl)-4,4-dimethyl-2-(1H-1,2,4-triazol-1-yl)-1-penten-3-ol,
(157) isopropyl 3,4-diethoxyphenylcarbamate,
(158) N-[4-chloro-2-fluoro-5-(1-methyl-2-propynyloxy)phenyl]-3,4,5,6-tetrahydrophthalimide,
(159) N-[4-chloro-2-fluoro-5-(pentyloxycarbonylmethoxy)phenyl]-3,4,5,6-tetrahydrophthalimide,
(160) 7-fluoro-6-(3,4,5,6-tetrahydrophthalimide)-4-(2-propynyl)-3,4-dihydro-1,4-benzoxazin-3(2H)-one,
(161) 2-[1-(ethoxyimino)ethyl]-3-hydroxy-5-[2-[4-(trifluoromethyl)phenylthio]ethyl]-2-cyclohexen-1-one,
(162) 1-(4-chlorophenyl)-3-(2,6-difluorobenzoyl)urea,
(163) isopropyl (2E,4E)-11-methoxy-3,7,11-trimethyl-2,4-dodecadienoate,
(164) 2-tert-butylimino-3-isopropyl-5-phenyl-3,4,5,6-tetrahydro-2H-1,3,5-thiadiazin-4-one,
(165) 2-phenoxy-6-(neopentyloxymethyl)pyridine,
(166) 3-chloro-2-[7-fluoro-4-(2-propynyl)-3,4-dihydro-1,4-benzoxazin-3(2H)-on-6-yl]-4,5,6,7-tetrahydro-2H-indazole,
(167) 4'-chloro-2'-(α-hydroxybenzyl)isonicotinanilide,
(168) 6-(benzylamino)pyrine,
(169) 5-chloro-3-methyl-4-nitro-1H-pyrazole,
(170) 2-chloroethyltrimethylammonium chloride,
(171) 2-(3-chlorophenoxy)propionic acid,
(172) 3-(4-chlorophenyl)-1,1-dimethylurea,
(173) 2,4-dichlorophenoxyacetic acid,
(174) 3-(3,4-dichlorophenyl)-1,1-dimethylurea,
(175) 1,1'-ethylene-2,2'-bipyridinium dibromide,
(176) maleic hydrazide,
(177) 2,4-dinitro-6-sec-butylphenol,
(178) 2,4-dimethyl-5-(trifluoromethylsulfonylamino)-acetanilide,
(179) 6-(furfurylamino)purine,
(180) β-hydroxyethylhydrazine,
(181) 3-indoleacetic acid,
(182) 3-methyl-5-(1-hydroxy-4-oxo-2,6,6-trimethyl-2-cyclohexen-1-yl) cis, trans-2,4-pentadienic acid,
(183) 1-naphthoxyacetic acid,
(184) 7-oxabicyclo[2.2.1]heptane-2,3-dicarboxylic acid monoalkylamine salt,
(185) 1-phenyl-3-[4-(2-chloropyridyl)]urea,
(186) sodium 5-chloro-1H-indazol-3-ylacetate,
(187) S,S-dimethyl 2-(difluoromethyl)-4-(2-methylpropyl)-6 -(trifluoromethyl)pyridine-3,5-dicarbothioate
(188) 3-(4,6-dimethoxy-1,3,5-triazin-2-yl)-1-[2-(2-methoxyethoxy)phenylsulfonyl]urea,
(189) exo-1-methyl-4-(1-methylethyl)-2-(2-methylphenylmethoxy)-7-oxabicyclo[2.2.1]heptane,
(190) 2',6'-diethyl-N-[(2-cis-butenoxy)methyl]2-chloroacetanilide,
(191) 2,3-dihydro-3,3-dimethyl-5-benzofuranyl ethanesulfonate,
(192) 2',6'-dimethyl-N-(3-methoxy-2-thenyl)-2-chloroacetanilide,
(193) 1-(2-chloroimidazo[1,2-a]pyridin-3-ylsulfonyl)-3-(4,6-dimethoxy-2-pyrimidinyl)urea,
(194) 3-isopropyl-1H-2,1,3-benzothiadiazin-4-(3H)-one-2,2-dioxide,
(195) 2-(1-ethoxyiminobutyl)-5-[2-(ethylthio)propyl]-(3-hydroxycyclohex-2-en-1-one, 2',6'-diethyl-N-(2-propoxyethyl)-2-chloroacetanilide,
(196) 2',6'-diethyl-N-(2-propoxyethyl)-2-chloroacetanilide,
(197) 1,1'-dimethyl-4,4'-bipyridinium dichloride,
(198) S-(1-methyl-1-phenylethyl) piperidine-1-carbothioate,
(199) S-(2-methyl-1-piperidinecarbonylmethyl) O,O-dipropyl dithiophosphate,
(200) S-behzyl N-ethyl-N-(1,2-dimethylpropyl)thiolcarbmate,
(201) 2-chloro-4-ethylamino-6-isopropylamino-1,3,5-triazine,
(202) 2-methylthio-4,5-bis(ethylamino)-1,3,5-triazine,
(203) ammonium homoalanin-4-yl(methyl)phosphinate,
(204) 2-chloro-4,6-bis(ethylamino)-1,3,5-triazine,
(205) sodium L-2-amino-4-[(hydroxy)(methyl)phosphinoyl]butyryl-L-alanyl-L-alaninate,
(206) isopropylammonium N-(phosphonomethyl)glycinate, (207) trimethylsulfonium N-(phosphonomethyl)glycinate,
(208) 2-methylthio-4-ethylamino-6-(1,2-dimethylpropylamino)-1,3,5-triazine,
(209) succinic 2,2-dimethylhydrazide, and
(210) 3-[2-(3,5-dimethyl-2-oxocyclohexyl)-2-hydroxymethyl]glutarimide.

In the composition according to the present invention, the addition of a calcined product precipitated hydrated silicon dioxide produced by the wet process or a silica produced by the dry process is preferred when the active ingredient has a melting point of lower than 70° C. That is, additives such as water-soluble carriers, water-soluble polymers, mineral carriers, solvents, lubricants or disintegrating agents are incorporated in addition to the essential active ingredient, the surface active agent, the carbonate, the solid acid and boron oxide and/or metaboric acid according to necessity.

In the composition according to the present invention, the pesticidal active ingredients may be used alone or in admixture of the two or more of them with an optional mixing ratio. The contents of these active ingredients vary depending on the kinds of the ingredients and are in the range of 0.01–80% by weight, preferably 0.1–50% by weight in proportion to the total weight of the composition of the present invention. In addition, when these active ingredients are liquids or are employed in the form of a solution in a solvent, the calcined product of precipitated hydrated silicon dioxide produced by the wet process or the silica produced by the dry process exhibit only insufficient effect as an oil absorbing agent at a content of the liquid ingredient containing the solvent exceeding 60% by weight to the total weight of the composition of the present invention. Thus, the content of the liquid ingredient should be usually in the range of 0.01–60% by weight, preferably 0.1–40% by weight.

The amount added to the calcined product of precipitated hydrated silicon dioxide produced by the wet process or the silica produced by the dry process is usually in the range of 50–200% by weight, preferably 60–100% by weight to the total liquid ingredient which is a liquid active ingredient or a solution in a solvent. For example, a synthetic hydrated silicon dioxide (silica produced by the wet process) such as Tokusil G-UN, Tokusil P, Tokusil U, Tokusil N (manufactured by Tokuyama Soda Co., Ltd.), Carplex #80 (manufactured by Shionogi & Co., Ltd.) Carplex #67, Carplex #1120, Carplex #100, Carplex #22S, Carplex FPS-1, Carplex FPS-2, Carplex FPS-3, Carplex FPS-4, Nipsil (manufactured by Nippon Silica) or Ultrasil (manufactured by Degussa) calcined at a temperature of 700°–900° C., preferably 800°–900° C. is used as a calcined product of a silica produced by the wet process. Commercially available products such as Carplex CS-5, Carplex CS-7 or Finisil P-8 (manufactured by Tokuyama Soda Co., Ltd.) may be used as such. On the other hand, as a silica produced by the dry process, there is employed a light silicic anhydride such as AEROSIL 200 or AEROSIL 300 (manufactured by Degussa).

Furthermore, when the active ingredient has a melting point in the range of 0°–70° C., a solvent is added, if necessary, in order to decrease the viscosity of the ingredient at its production and to prevent the crystallization of the active ingredient upon storage at a low temperature. As the solvent, there is usually used a nonvolatile or sparingly volatile organic solvent. The solvents used for regulating viscosity and preventing crystallization of the active ingredients include those which are homogeneously mixed with the active ingredients, for example, aromatic hydrocarbons such as phenylxylethane ketones, negetable oils, mineral oils, liquid paraffin, polyethylene glycol having an average molecular weight in the range of about 200–600 which is liquid at room temperature, polypropylene glycol, and glycol ether such as polypropylene glycol methyl ether and acetate thereof, particularly phenylxylylethane, glycol ethers and acetates of glycol ethers are preferred.

The added amount of the solvent is usually in the range of 10–1000% by weight, preferably 30–200% by weight to the amount of the active ingredient. The aforementioned solvent may be added, if necessary, for lowering the viscosity at production, even if the active ingredient has a melting point of 0° C. or less.

As the surface active agents used in the present invention, there can be mentioned anionic surface active agents such as alkyl aryl sulfonates, alkyl naphthalene sulfonates, lignin sulfonates, dialkyl sulfosuccinates, polyoxyethylene alkyl aryl ether sulfates, alkali metal salts of copolymers having carboxyl groups and fatty acid salts and noinoic surface active agents such as polyoxyethylene alkyl ethers, polyoxyethylene alkyl phenyl ethers, polyoxyethylene styryl phenyl ethers, polyoxyethylene alkyl esters, sorbitan alkyl esters and polyoxyethylene sorbitan alkyl esters which are able to emulsify and disperse the active ingredient and the calcined silica according to the wet process. Also, there may be used cathionic surface active agents, or amphoteric surface active agents according to necessity. These surface active agents are used alone or in admixture of the two or more. The used amount of the surface active agent is usually in a proportion of 0.1–70% by weight, preferably 1–40% by weight, more preferably 3–20% by weight, to the total weight of the composition of the present invention.

As the carbonate used in the composition of the present invention, there are mentioned for example sodium carbonate, potassium carbonate, lithium carbonate, ammonium carbonate, calcium carbonate, sodium bicarbonate, potassium bicarbonate, lithium bicarbonate, ammonium bicarbonate, potassium sesquicarbonate and ammonium sesquicarbonate. Sodium bicarbonate or sodium carbonate is particularly preferred. The aforementioned carbonates are used alone or as a mixture of the two or more at any ratios.

As the solid acid used in the composition of the present invention, there are mentioned for example citric acid, succinic acid, maleic acid, fumaric acid, tartaric acid, oxalic acid, malonic acid, malic acid, adipic acid, boric acid, sodium dihydrogen phosphate, potassium dihydrogen phosphate, benzoic acid, sulfamic acid, salicylic acid, ascobic acid, glutamic acid, asparatic acid, sorbic acid, nicotinic acid and phenylacetic acid. Particularly, maleic acid, fumaric acid, citric acid, succinic acid, boric acid, malic acid and tartaric acid are preferred. These acids are used alone or as a mixture of the two or more at any ratios.

The total amount of the carbonate and the solid acid used is usually in a proportion of 5–90% by weight, preferably 10–70% by weight, more preferably 20–60% by weight to the total weight of the composition of the present invention. The weight ratio of the carbonate to the solid acid is usually in a range of 1:10–10:1, preferably 1:5–5:1, more preferably 1:3–3:1.

Boron oxide and metaboric acid used in the present invention can be used alone or as a mixture of the two or more at any ratios.

Also, as the water-soluble carrier, the water-soluble polymer, the mineral carrier, the lubricant and the disintegrating agent, there are mentioned the following materials.

First of all, as the water-soluble carrier, there are mentioned urea, lactose, ammonium sulfate, sugar, sodium chloride and sodium sulfate.

As the water-soluble polymer, there are mentioned hydroxypropyl cellulose, methyl cellulose, methylethyl cellulose, polyvinyl alcohol, polyvinyl pyrrolidone, hydroxypropylmethyl cellulose, sodium carbonxymethyl cellulose, and polyethylene glycols having an average molecular weight of 6000–20000.

As the mineral carrier, there are mentioned kaolin clay, diatomite, acid clay, talc and attapulgite clay.

Moreover, the lubricant includes magnesium stearate, or titanium oxide, and the disintegrating agent includes microcrystalline cellulose.

When these water-soluble carrier, water-soluble polymer, mineral carrier, lubricant and disintegrating agent are added, the amount added is usually in a proportion of 0.1–50% by weight, preferably 0.5–20% by weight to the total weight of the composition of the present invention.

Furthermore, it is also possible to add appropriately a stabilizer, an effect stimulating agent, a colorant, a perfume, or a builder to the composition of the present invention.

The composition according to the present invention, of which active ingredient has a melting point of 70° C. or more, can be produced by pulverizing the active ingredient alone or a mixture of it with either one or all of the surface active agent, the carbonate and the solid acid with a dry pulverizer such as air mill, pinmill or hammer mill, and then mixing them with the residual ingredients. When the active ingredient is liquid or in the form of liquid by the addition of a solvent, the composition may be produced in the same manner as above after the active ingredient is absorbed into the calcined product of silica produced by the wet process or the silica produced by the dry process.

The powderous composition of the present invention obtained thus can be used as such, but it is desirable to us it in the form of granule or tablet in consideration of its handling, safety or environmental effect. In this connection, the granule means the granulated product of the powderous composition of the present invention, of which shape varies depending on granulation methods and is in a wide range of cylindricals, sphericals or irregulars. Also, the tablet means a product of the powderous or glanular composition of the present invention compressed into a certain shape, which is in a variety from the ones having sharp edges or rounded edges to the one of a lens having shallow curvature, such as a pillow shape, an almond shape, a finger shape, triangle, square, pentagon or a capsule shape.

The granule can be prepared by forming the powderous composition of the present invention into a granulated product in the form of sheet, pillow or slugs with a dry granulating machine such a roll compactor or a briquetting machine or with a slug machine, respectively, and breaking the granulated product or slugs with a screening apparatus. In this connection, the granule is preferably subjected to sphering treatment with a Marumerizer (Produced by Fuji Paudal Co., Ltd.) or the like in order to prevent dusting on its transport or use. If the compacting machine is used, the powderous composition is placed between rotary rolls and is pressed at 30 kg/cm$^2$ or more, preferably 50 kg/cm$^2$ or more. This method uses no water, and carbon dioxide gas is not generated during the production process, so that when the granule is applied to a paddy field, a pond or a river or diluted with water, effervescence is observed more sufficiently.

The aforementioned granule has usually a particle diameter in the range of about 10000–100 μm, preferably about 4000–297 μm.

The tablet may be prepared by tableting a certain amount of the powderous composition of the present invention by hand. In an industrial scale, tablets having a certain weight can be continuously prepared by tableting the aforementioned powder or granule in a tableting machine or a briquetting machine.

The tablet may be in the sizes suitable for its applications and usually has a diameter in the range of about 7–60 mm, a thickness in the range of about 1–40 mm and a weight in the range of about 0.1–100 g, preferably about 1–50 g.

The composition of the present invention is directly applied to an irrigated paddy field, a river, a pond, a field, a lawn, an orchard, a non-cultivated field, or it is used as an appropriate dilution with water.

When the composition of the present invention is applied to an irrigated paddy field, the applied amount thereof varies depending on the kinds or amounts of the active ingredients and is usually in the range of about 50–2000 g, preferably about 500–1000 g per 10 are.

When the composition of the present invention is applied directly, no special devices are generally required. For instance, an operator gets into a paddy field and applies the composition of the present invention uniformly or to one or more places of the paddy field, or he applies the composition to the sides of the footpaths of the paddy field or to the water inlet of the paddy field or distributes the composition from the footpaths without getting into the paddy field, so that the active ingredient can be distributed and diffused to all of the paddy field. Also, the composition can be applied by a motorized granular application at a footpath or dispersed into air with a helicopter, an airplane or a radiocontrolled airplane.

When the composition of the present invention is applied to an irrigated paddy field, a pond or a river, it moves by the generation of carbon dioxide gas and the active ingredient is rapidly and uniformly diffused into water. Thus the pesticidal ingredient against pests, harmful microorganisms or weeds exhibits sufficient effects on pests or crops, respectively, and is diffused uniformly, so that the composition of the present invention is also a composition excellent in the point of reducing the phytotoxicity of pesticides. Also, when the composition of the present invention is applied to a paddy field, the applied amount thereof can be reduced extensively, so that the composition is also useful in the points of the production, transport, storage and labor-saving dispersion of the product. Furthermore, when the composition of the present invention is used as a dilution with water, it generates carbon dioxide gas in water and thus is disintegrated, dispersed or emulsified easily, so that it can be handled conveniently.

The present invention is further explained in detail with reference to preparation examples, comparative examples and test examples, but it is not limited thereto.

In addition, parts in the preparation examples and the comparative examples indicate parts by weight.

First of all, preparation examples are described.

PREPARATIVE EXAMPLE 1

20 parts of the compound (128), 4.5 parts of REAX 85A (sodium lignin sulfonate, manufactured by Westvaco), 0.5 part of REAX 88B (sodium lignin sulfonate, manufactured by Westvaco), 5 parts of GEROPON SC-211 (potassium salt of a copolymer having carboxyl groups, manufactured by Rhone Poulenc), 10 parts of boron oxide, 30 parts of sodium carbonate and 30 parts of maleic acid were mixed well in a juice mixer and then pulverized in a centrifugal pulverizer. The mixture was next granulated into a granular sheet under a pressure of 50 kg/cm$^2$ using a roll compactor TF-MINI (mfg. by Freund Sangyo K. K.) and then broken using pestle and mortar and screened for obtaining granule having a particle diameter in the range of 1000–297 μm.

Preparation Example 2

The granule having a particle diameter in the range of 1680–1000 μm was prepared by the same operation in the same composition as Preparation Example 1.

Preparation Example 3

The same procedure as in Preparation Example 1 was repeated with 20 parts of the compound (128), 9 parts of REAX 85A, 1 part of REAX 88B, 5 parts of GEROPON SC-211, 5 parts of boron oxide, 30 parts of sodium carbonate and 30 parts of maleic acid to give granules having a diameter of 1000–297 μm.

Preparation Example 4

The same procedure as in Preparation Example 1 was repeated with 20 parts of the compound (128), 11.25 parts of REAX 85A, 1.25 part of REAX 88B, 5 parts of GEROPON SC-211, 2.5 parts of boron oxide, 30 parts of sodium carbonate and 30 parts of maleic acid to give granules having a diameter of 1000–297 μm.

Preparation Example 5

The same procedure as in Preparation Example 1 was repeated with 20 parts of the compound (128), 4.5 parts of REAX 85A, 0.5 part of REAX 88B, 5 parts of GEROPON SC-211, 10 parts of metaboric acid, 30 parts of sodium carbonate and 30 parts of maleic acid to give granules having a diameter of 1000–297 μm.

Preparation Example 6

The same procedure as in Preparation Example 1 was repeated with 20 parts of the compound (128), 9 parts of REAX 85A, 1 part of REAX 88B, 5 parts of metaboric acid, 5 parts of lactose, 30 parts of sodium carbonate and 30 parts of maleic acid to give granules having a diameter of 1000–297 μm.

Preparation Example 7

The same procedure as in Preparation Example 1 was repeated with 6 parts of the compound (97), 22.5 parts of REAX 85A, 1.5 parts of REAX 88B, 5 parts of GEROPON SC-211, 5 parts of boron oxide, 30 parts of sodium carbonate and 30 parts of maleic acid to give granules having a diameter of 1000–297 μm.

Preparation Example 8

The same procedure as in Preparation Example 1 was repeated with 6 parts of the compound (97), 22.5 parts of REAX 85A, 1.5 parts of REAX 88B, 5 parts of GEROPON SC-211, 5 parts of metaboric acid, 30 parts of sodium carbonate and 30 parts of maleic acid to give granules having a diameter of 1000–297 μm.

Preparation Example 9

The same procedure as in Preparation Example 1 was repeated with 0.2 part of the compound (126), 31.8 parts of REAX 85A, 3 parts of REAX 88B, 5 parts of boron oxide, 30 parts of sodium carbonate and 30 parts of maleic acid to give granules having a diameter of 1000–297 μm.

Preparation Example 10

The same procedure as in Preparation Example 1 was repeated with 0.1 part of the compound (126), 26.9 parts of REAX 85A, 3 parts of REAX 88B, 5 parts of GEROPON SC-211, 5 parts of boron oxide, 30 parts of sodium carbonate and 30 parts of maleic acid to give granules having a diameter of 1000–297 μm.

Preparation Example 11

The same procedure as in Preparation Example 1 was repeated with 0.2 part of the compound (126), 13.5 parts of REAX 85A, 1.5 parts of REAX 88B, 5 parts of boron oxide, 49.8 parts of sodium carbonate and 30 parts of maleic acid to give granules having a diameter of 1000–297 μm.

Preparation Example 12

The same procedure as in Preparation Example 1 was repeated with 8 parts of the compound (164), 20.5 parts of REAX 85A, 1.5 parts of REAX 88B, 5 parts of GEROPON SC-211, 5 parts of boron oxide, 30 parts of sodium carbonate and 30 parts of maleic acid to give granules having a diameter of 1000–297 μm.

Preparation Example 13

The same procedure as in Preparation Example 1 was repeated with 50 parts of the compound (155), 13 parts of MORWET D425 (formaldehyde condensate of sodium naphthalene sulfonate, manufactured by DESOTO), 2 parts of Sorpol 5029-o (sodium alkylsulfate, manufactured by TOHO KAGAKU K. K.), 5 parts of metaboric acid, 15 parts of sodium bicarbonate and 15 parts of fumaric acid to give granules having a diameter of 1000–297 μm.

Preparation Example 14

2 parts of the compound (165), 2 parts of polyoxyethylene (20) sorbitan monolaurate, 10 parts of boron oxide, 40 parts of sodium bicarbonate and 46 parts of maleic acid were mixed with a mortar and a pestle and further mixed well in a juice mixer. The mixture was next pressed at a pressure of 150 kg/cm$^2$ with a roll compactor TF-MINI model to form a granulated sheet, which was then broken with a mortar and a pestle and passed through a screen to give granules having a particle diameter of 1000–297 μm.

Preparation Example 15

The same procedure as in Preparation Example 14 was repeated with 2 parts of the compound (165), 2 parts of polyoxyethylene (10) nonyl phenyl ether, 10 parts of boron oxide, 40 parts of sodium bicarbonate and 46 parts of maleic acid to give granules having a diameter of 1000–297 μm.

Preparation Example 16

The same procedure as in Preparation Example 14 was repeated with 5 parts of the compound (125), 5 parts of phenylxylylethane, 10 parts of Carplex CS-7 (a calcined product of silica produced by the wet process, manufactured by Shionogi & Co., Ltd.), 5 parts of boron oxide, 12 parts of a spray-dried product of sodium dodecylbenzenesulfonate:Carplex CS-7=1:1 (Carplex CS-7 was dispersed into an aqueous solution of sodium dodecylbenzenesulfonate and then the mixture was spray-dried with a spray-dryer to form powder), 3 parts of DEMOL SN-B (formaldehyde condensate sodium naphthalene sulfonate, manufactured by Kao Soap Co., Ltd.), 30 parts of sodium carbonate and 30 parts of maleic acid to give granules having a diameter of 1000–297 μm.

Preparation Example 17

The same procedure as in Preparation Example 14 was repeated with 5 parts of the compound (125), 10 parts of phenylxylylethane, 11 parts of Carplex CS-7, 10 parts of boron oxide, 10 parts of a spray-dried product of sodium dodecylbenzenesulfonate:Carplex CS-7=1:1, 3 parts of DEMOL SN-B, 21 parts of lactose, 15 parts of sodium carbonate and 15 parts of maleic acid to give granules having a diameter of 1000–297 μm.

Preparation Example 18

The same procedure as in Preparation Example 14 was repeated with 5 parts of the compound (125), 10 parts of phenylxylylethane, 11 parts a Carplex CS-7, 10 parts of boron oxide, 9 parts of REAX 85A, 1 part of REAX 85B, 5 parts of GEROPON SC-211, 19 parts of lactose, 15 parts of sodium carbonate and 15 parts of maleic acid to give granules having a diameter of 1000–297 μm.

Preparation Example 19

The same procedure as in Preparation Example 14 was repeated with 5 parts of the compound (125), 10 parts of phenylxylylethane, 11 parts of Carplex CS-7, 10 parts of boron oxide, 10 parts of a spray-dried product of sodium dodecylbenzenesulfonate:Carplex CS-7=1:1, 3 parts of DEMOL SN-B, 5 parts of polyethylene glycol (average molecular weight, 20000), 16 parts of calcined diatomite, 15 parts of sodium carbonate and 15 parts of maleic acid to give granules having a diameter of 1000–2297 μm.

Preparation Example 20

The same procedure as in Preparation Example 14 was repeated with 5 parts of the compound (125), 10 parts of phenylxylylethane, 11 parts of AEROSIL 200 (silica produced by the dry process, manufactured by Degussa), 10 parts of boron oxide, 9 parts of REAX 85A, 1 part of REAX 85B, 5 parts of GEROPON SC-211, 19 parts of lactose, 15 parts of sodium carbonate and 15 parts of maleic acid to give granules having a diameter of 1000–297 μm.

Preparation Example 21

The same procedure as in Preparation Example 14 was repeated with 10 parts of the compound (3), 20 parts of phenylxylylethane, 22 parts of Carplex CS-7, 5 parts of boron oxide, 10 parts of a spray-dried product of sodium dodecylbenzenesulfonate:Carplex CS-7=1:1, 3 parts of DEMOL SN-B, 22.5 parts of sodium bicarbonate and 7.5 parts of maleic acid to give granules having a diameter of 1000–297 μm.

Preparation Example 22

The same procedure as in Preparation Example 14 was repeated with 10 parts of the compound (3), 20 parts of phenylxylylethane, 22 parts of Carplex CS-7, 5 parts of boron oxide, 10 parts of a spray-dried product of sodium dodecylbenzenesulfonate:Carplex CS-7=1:1, 3 parts of DEMOL SN-B, 20 parts of sodium bicarbonate and 10 parts of maleic acid to give granules having a diameter of 1000–297 μm.

Preparation Example 23

The same procedure as in Preparation Example 14 was repeated with 10 parts of the compound (3), 20 parts of phenylxylylethane, 22 parts of Carplex CS-7, 5 parts of boron oxide, 10 parts of a spray-dried product of sodium dodecylbenzenesulfonate:Carplex CS-7=1:1, 3 parts of DEMOL SN-B, 15 parts of sodium bicarbonate and 10 parts of maleic acid to give granules having a diameter of 1000–297 μm.

Preparation Example 24

The same procedure as in Preparation Example 14 was repeated with 10 parts of the compound (3), 20 parts of phenylxylylethane, 22 parts of Carplex CS-7, 5 parts of boron oxide, 10 parts of a spray-dried product of sodium dodecylbenzenesulfonate:Carplex CS-7=1:1, 3 parts of DEMOL SN-B, 10 parts of sodium bicarbonate and 20 parts of maleic acid to give granules having a diameter of 1000–297 μm.

Preparation Example 25

The same procedure as in Preparation Example 14 was repeated with 10 parts of the compound (3), 20 parts of phenylxylylethane, 22 parts of Carplex CS-7, 5 parts of boron oxide, 10 parts of a spray-dried product of sodium dodecylbenzenesulfonate:Carplex CS-7=1:1, 3 parts of DEMOL SN-B, 7.5 parts of sodium bicarbonate and 22.5 parts of maleic acid to give granules having a diameter of 1000–297 μm.

Preparation Example 26

The same procedure as in Preparation Example 14 was repeated with 5 parts of the compound (3), 5 parts of the compound (34), 7 parts of Carplex CS-7, 5 parts of boron oxide, 10 parts of a spray-dried product of sodium dodecylbenzenesulfonate:Carplex CS-7=1:1, 3 parts of DEMOL SN-B, 35 parts of lactose, 15 parts of sodium carbonate and 15 parts of maleic acid to give granules having a diameter of 1000–297 μm.

Preparation Example 27

A 2.5 g portion of the granule obtained in Preparation Example 1 was placed in a tableting machine having a diameter of 30 mm and punched at a pressure of 500 kg/cm$^2$ to give tablets.

Preparation Example 28

A 5 g portion of the granule obtained in Preparation Example 5 was placed in a tableting machine having a diameter of 30 mm and punched at a pressure of 500 kg/cm$^2$ to give tablets.

Preparation Example 29

A 5 g portion of the granule obtained in Preparation Example 1 was placed in a tableting machine having a diameter of 30 mm and punched at a pressure of 500 kg/cm² to give tablets.

Preparation Example 30

A 1 g portion of the powder which was intended to be granulated in Preparation Example 17 was placed in a tableting machine having a diameter of 20 mm and punched at a pressure of 500 kg/cm² to give tablets.

Preparation Example 31

A 0.5 g portion of the powder which was intended to be granulated in Preparation Example 26 was placed in a tableting machine having a diameter of 10 mm and punched at a pressure of 300 kg/cm² to give tablets.

Preparation Example 32

The same composition as in Preparation Example 1 was used and the same operations as in Preparation Example 1 were conducted to give granules having a particle diameter of 4000–297 μm.

Preparation Example 33

The same procedure as in Preparation Example 1 was repeated with 20 parts of the compound (154), 4.5 parts of REAX 85A, 0.5 part of REAX 88B, 5 parts of GEROPON SC-211, 5 parts of boron oxide, 5 parts of calcium carbonate, 30 parts of sodium carbonate, and 30 parts of maleic acid to give granules having a particle diameter of 1000–297 μm.

Preparation Example 34

9 parts of the compounds (128), 8 parts of Carplex CS-7, 5 parts of boron oxide, 10 parts of a spray-dried product of sodium dodecylbenzene sulfonate:Carplex CS-7=1:1, 3 parts of DEMOL SN-B, 25 parts of sodium carbonate, 25 parts of maleic acid and 4.5 parts of lactose were mixed well in a juice mixer and then pulverized in a centrifugal pulverizer. After the mixture was placed in a mortar and 10.5 parts of the compound (123) was added to and mixed with the product with a pestle, the mixture was mixed well with a juice mixer. The mixture was formed into a granulated sheet at a pressure of 150 kg/cm² with a roll compactor TF-MINI model, broken with a mortar and a pestle and passed through a screen to give granules having a particle diameter of 1680–710 μm.

Preparation Example 36

The same composition as in Preparation Example 35 was used and the same operations as in Preparation Example 35 were conducted to give granules having a particle diameter of 2000–1000 μm.

Preparation Example 37

The same composition as in Preparation Example 35 was used and the same operations as in Preparation Example 35 were conducted to give granules having a particle diameter of 2800–1680 μm.

Preparation Example 38

The same procedure was repeated as in Preparation Example 35 except that 5 parts of metaboric acid was used in place of 5 parts of boron oxide to give granules having a particle diameter of 1680–710 μm.

Preparation Example 39

The same procedure was repeated as in Preparation Example 35 except that 15 parts instead of 25 parts of sodium carbonate, 15 parts instead of maleic acid and 24.5 parts instead of 4.5 parts of lactose to give granules having a particle diameter of 1680–710 μm.

Preparation Example 40

The same procedure was repeated as in Preparation Example 39 except that 5 parts of metaboric acid was used in place of 5 parts of boron oxide to give granules having a particle diameter of 1680–710 μm.

Preparation Example 41

The same procedure was repeated as in Preparation Example 39 except that 15 parts of boric acid was used in place of 5 parts of maleic acid to give granules having a particle diameter of 1680–710 μm.

Preparation Example 42

The same procedure was repeated as in Preparation Example 39 except that 15 parts of citric acid was used in place of 5 parts of maleic acid to give granules having a particle diameter of 1680–710 μm.

Preparation Example 43

The same procedure as in Preparation Example 35 was repeated with 9 parts of the compound (128), 8 parts of Carplex CS-7, 5 parts of boron oxide, 15 parts of GEROPON SC-211, 25 parts of sodium carbonate, 25 parts of maleic acid, 2.5 parts of lactose and 10.5 parts of the compound (123) to give granules having a particle diameter of 1680–71.0 μm.

Preparation Example 44

The same procedure as in Preparation Example 35 was repeated with 9 parts of the compound (123), 8 parts of Carplex CS-7, 10 parts of boron oxide, 15 parts of GEROPON SC-211, 15 parts of sodium carbonate, 15 parts of maleic acid, 17.5 parts of lactose and 10.5 parts of the compound (123) to give granules having a particle diameter of 1680–710 μm.

Comparative Examples are described below.

Comparative Example 1

The same procedure as in Preparation Example 1 was repeated with 20 parts of the compound (82), 9 parts of REAX 85A, 1 part of REAX 85B, 10 parts of lactose, 30 parts of sodium carbonate and 30 parts of maleic acid to give granules having a particle diameter of 1000–297 μm.

Comparative Example 2

The same procedure as in Preparation Example 1 was repeated with 0.2 part of the compound (126), 36.8 parts of REAX 85A, 3 parts of REAX 85B, 30 parts of sodium carbonate and 30 parts of maleic acid to give granules having a particle diameter of 1000–297 μm.

Comparative Example 3

The same procedure as in Preparation Example 1 was repeated with 20 parts of the compound (154), 5 parts of GEROPON SC-211, 30 parts of sodium carbonate and 30 parts of maleic acid to give granules having a particle diameter of 1000–297 μm.

Comparative Example 4

The same procedure as in Preparation Example 14 was repeated with 5 parts of the compound (125), 5 part of phenylxylylethane, 11 parts of Carplex #8 (an uncalcined silica produced by the wet process, manufactured by Shionogi & Co., Ltd.), 10 parts of Sorpol 5060 (a spray-dried product of sodium dodecylbenzene sulfonate:powderous hydric silicic acid=1:1, Toho Kagaku K. K.), 3 parts of DEMOL SN-B, 31 parts of lactose, 15 parts of sodium carbonate and 15 parts of maleic acid to give granules having a diameter of 1000–297 μm.

Comparative Example 5

The same procedure as in Preparation Example 14 was repeated with 10 parts of the compound (3), 20 parts of phenylxylylethane, 22 parts of Carplex #8, 10 parts of Sorpol 5060, 3 parts of DEMOL SN-B, 22.5 parts of sodium carbonate and 7.5 parts of maleic acid to give granules having a diameter of 1000–297 μm.

Comparative Example 6

The same procedure as in Preparation Example 14 was repeated with 10 parts of the compound (3), 20 parts of phenylxylylethane, 22 parts of Carplex #8, 5 parts of lactose, 10 parts of Sorpol 5060, 3 parts of DEMOL SN-B, 20 parts of sodium bicarbonate and 10 parts of maleic acid to give granules having a diameter of 1000–297 μm.

Comparative Example 7

The same procedure as in Preparation Example 14 was repeated with 10 parts of the compound (3), 20 parts of phenylxylylethane, 22 parts of Carplex #8, 5 parts of lactose, 10 parts of Sorpol 5060, 3 parts of DEMOL SN-B, 15 parts of sodium bicarbonate and 15 parts of maleic acid to give granules having a diameter of 1000–297 μm.

Comparative Example 8

The same procedure as in Preparation Example 14 was repeated with 10 parts of the compound (3), 20 parts of phenylxylylethane, 22 parts of Carplex #8, 5 parts of lactose, 10 parts of Sorpol 5060, 3 parts of DEMOL SN-B, 10 parts of sodium bicarbonate and 20 parts of maleic acid to give granules having a diameter of 1000–297 μm.

Comparative Example 9

The same procedure as in Preparation Example 14 was repeated with 10 parts of the compound (3), 20 parts of phenylxylylethane, 22 parts of Carplex #8, 5 parts of lactose, 10 parts of Sorpol 5060, 3 parts of DEMOL SN-B, 7.5 parts of sodium bicarbonate and 22.5 parts of maleic acid to give granules having a diameter of 1000–297 μm.

Comparative Example 10

4 parts of the compound (128), 4 parts of Sorpol 5060, 30 parts of bentonite clay and 62 parts of kaolin clay were mixed well in a juice mixer and then pulverized in a centrifugal pulverizer. Then, 15 parts of water was added to the mixture, and the resulting mixture was kneaded with a mortar and a pestle, subjected to granulation and screening in an extrusion granulator equipped with a screen having a diameter of 0.9 mm and dried at 60° C. for 10 minutes to give particles having a particle diameter of 1680–297 μm.

Comparative Example 11

1 part of the compound (165) and 2 parts of Sorpol 3598 (surface active agent, manufactured by Toho Kagaku K. K.) were mixed, then added to 97 parts of ISHIKAWA LITE #3 (porous granular carrier, manufactured by Ishikawa LITE K. K.) and mixed well to give particles.

Comparative Example 12

The same procedure as in Preparation Example 14 was repeated with 10 parts of the compound (3), 20 parts of phenylxylylethane, 22 parts of Carplex #80, 35 parts of lactose, 10 parts of Sorpol 5060 and 3 parts of Demol SN-B to give granules having a particle diameter of 1000–297 μm.

Comparative Example 13

The same procedure as in Preparation Example 1 was repeated with 20 parts of the compound (128), 9 parts of REAX 85A, 1 part of REAX 85B, 10 parts of anhydrous sodium sulfate, 30 parts of sodium carbonate and 30 parts of maleic acid to give granules having a particle diameter of 1000–297 μm.

Test Examples are described below.

Test Example 1

About 1 g of each composition obtained in Preparation Examples 1–31, 33 and 34 and Comparative Examples 1–9 and 13 was packed in a polyethylene-laminated aluminium bag (length, 11.5 cm; width, 16.5 cm) and stored at 40° C. for 30 days and at 50° C. for 30 days, and the state of the bag was observed.

After store, the bag was opened by cutting it with scissors to get the gas generated out of the bag, and the total weight was measured to calculate the weight loss with the total weight and the weight of the formulation before storage by the following equation:

$$\text{Weight loss \%} = \frac{\text{Total weight before storage (g)} - \text{Total weight after storage (g)}}{\text{Weight of formulation before storage (g)}} \times 100$$

The results are shown in Table 1.

TABLE 1

| Test Composition | After storage at 40° C. for 30 days | | After storage at 50° C. for 30 days | |
| --- | --- | --- | --- | --- |
| | State of bag | Weight loss (%) | State of bag | Weight loss (%) |
| Preparation Example | | | | |
| 1 | — | 0 | — | 0 |
| 2 | — | 0 | — | 0 |
| 3 | — | 0 | — | 0.1 |
| 4 | — | 0 | — | 0.2 |
| 5 | — | 0 | — | 0.2 |
| 6 | — | 0 | — | 0.2 |
| 7 | — | 0 | — | 0 |
| 8 | — | 0 | | |
| 9 | — | 0 | | |
| 10 | — | 0 | | |
| 11 | — | 0.1 | | |
| 12 | — | 0 | | |
| 13 | — | 0 | | |
| 14 | — | 0 | | |
| 15 | — | 0 | | |
| 16 | — | 0 | — | 0.2 |
| 17 | — | 0 | — | 0.2 |
| 18 | — | 0 | — | 0.1 |
| 19 | — | 0 | — | 0.2 |
| 20 | — | 0 | — | 0 |
| 21 | — | 0 | — | 0 |
| 22 | — | 0 | — | 0 |
| 23 | — | 0 | — | 0.2 |
| 24 | — | 0 | — | 0.1 |
| 25 | — | 0 | — | 0.1 |

TABLE 1-continued

| Test Composition | After storage at 40° C. for 30 days | | After storage at 50° C. for 30 days | |
|---|---|---|---|---|
| | State of bag | Weight loss (%) | State of bag | Weight loss (%) |
| 26 | — | 0 | | |
| 27 | — | 0 | — | 0 |
| 28 | — | 0 | | |
| 29 | — | 0 | | |
| 30 | — | 0 | — | 0.1 |
| 31 | — | 0 | | |
| 33 | — | 0.1 | | |
| 34 | — | 0 | | |
| Comparative Example | | | | |
| 1 | + | 0.4 | +++ | 1.0 |
| 2 | + | 0.6 | | |
| 3 | + | 0.6 | | |
| 4 | +++ | 1.2 | +++ | 3.4 |
| 5 | + | 0.4 | + | 0.6 |
| 6 | + | 0.6 | + | 0.8 |
| 7 | +++ | 0.8 | +++ | 2.0 |
| 8 | + | 0.6 | +++ | 1.4 |
| 9 | + | 0.6 | +++ | 1.2 |
| 13 | + | 0.3 | +++ | 1.0 |

(Indices for indicating the states of the bag)
—: No change,
+: Slight expansion of bag,
++: Some expansion of bag,
+++: Largely expansion of bag.

Test Example 2

Three partition plates were arranged in an aluminium vat having a length of 35 cm and a width of 53 cm as shown in FIG. 1, and 7 liters of deionized water was charged in it. Next, the composition obtained in Preparation Example 3 having a content of the active ingredient corresponding to 100 g/10 are, the aforementioned composition having been stored under the condition described in Test Example 1, and the composition obtained in Comparative Example 10 were charged into the vat, respectively, and the distance of the movement of the composition was observed visually.

After 24 hours from the charge of the compositions, 25 ml of the liquid at the positions of the distances of 0 cm, 87 cm or 174 cm and at the depth of about 0.5 cm from the bottom was sampled with a transfer pipet, and water was evaporated. The residual sample was analyzed by a gas chromatograph (detector: ECD) to measure the amount of active ingredient.

The results are shown in Table 2.

TABLE 2

| Test Composition | Dispersibility | Amount of active ingredient in 25 ml of liquid (μm) | | |
|---|---|---|---|---|
| | | 0 cm | 87 cm | 147 cm |
| Preparation Example 3 (immediately after production) | A | 58.1 | 67.5 | 47.0 |
| Preparation Example 3 (after storage at 40° C. for 50 days) | A | 55.0 | 77.4 | 55.7 |
| Preparation Example 3 (after storage at 50° C. for 50 days) | A | 50.3 | 54.6 | 46.5 |
| Comparative Example 10 | D | 84.0 | 11.4 | 1.9 |

(Evaluation criteria of dispersibility)
Shift at a distance of 2 m or more: A, 1 m or more and less than 2 m: B, 50 cm or more and less than 1 m: C, less than 50 cm: D.

It is obvious from Table 2 that the composition of the present invention is excellent in dispersibility as compared with the conventional preparations illustrated by Comparative Examples and that the composition of the present invention is excellent in stability during storage.

Test Example 3

Into an aluminium vat used in Test Example 2 was poured the composition obtained in Preparation Examples 1, 2, 5, 7, 9 or 12 in an amount which corresponds to 750 g of the composition per 10 are. The distance of the movement of the composition was observed visually and its dispersibility was evaluated.

The results are listed in Table 3 (using the same evaluation criteria for dispersibility)

TABLE 3

| Test composition | Dispersibility |
|---|---|
| Preparation Example 1 | A |
| Preparation Example 2 | A |
| Preparation Example 5 | A |
| Preparation Example 7 | A |
| Preparation Example 9 | A |
| Preparation Example 12 | A |

Test Example 4

To the water surface around the root of a rice at a tillering period planted in a Wagner pot having an area of 1/10000 are was applied the composition obtained in Preparation Examples 14 and 15 and Comparative Example 11 in an amount of the active ingredient corresponding to 30 g/10 are. This was covered with a metal net basket, of which external side was covered with a polyethylene bag, in which 15 brown rice planthoppers were pastured and their life or death was examined after 24 hours.

TABLE 4

| Test composition | Mortality of brown rice plant hopper (%) |
|---|---|
| Preparation Example 14 | 100 |
| Preparation Example 15 | 97 |
| Comparative Example 11 | 36 |

Test Example 5

Self dispersibilities of the compositions obtained in Preparation Example 23 and Comparative Example 7, those having been stored under the condition described in Test Example 1 and the composition obtained in Comparative Example 12 were measured by the following method. In this connection, the self-dispersibility indicates the suspension rate of the active ingredient in the state without stirring.

A 250 ml volume cylinder with a co-stopper containing 250 ml of water having 3 H (hardness) at 20° C. was placed and 500 mg of each composition was charged through a funnel into the cylinder. A 25 ml portion of the sample was taken out of the center of the cylinder at 2 mm after dilution, the gas chromatographical analysis (detector: FID) was conducted to evaluate the self-dispersibility after water was evaporated.

The results are shown in Table 5.

TABLE 5

| Test Composition | Self-dispersibility (%) | | |
|---|---|---|---|
| | Immediately after production | After storage at 40° C. 30 days | After storage at 50° C. 30 days |
| Preparation Example 23 | 88.5 | 91.5 | 85.5 |
| Comparative Example 7 | 78.9 | 62.0 | 53.3 |
| Comparative Example 12 | 5.3 | — | — |

It is obvious from Table 5 that the composition of the present invention are excellent in self-dispersibility as compared with the non-effervescence composition described in Comparative Example 12 and are also excellent in storage stability as compared with the foaming composition described in Comparative Example 7.

In the accompanying drawing:

FIG. 1 is a plan view of an aluminium vat used in Experimental Examples 2 and 3, wherein three partitions are provided so that they are parallel to the longer side walls of the vat and the gap between the partitions and the shorter side walls is 9 cm. The mark X indicates the position at which the test composition is charged.

What is claimed is:

1. A pesticidal composition comprising a) a pesticidal active ingredient, b) a surface active agent, c) a carbonate, d) a solid acid and e) at least one selected from the group consisting of boron oxide and metaboric acid, wherein at least one of the carbonate and the solid acid is water-soluble, the total content of the carbonate and the solid acid is in a proportion of 5–9% to the total weight, the weight ratio of the carbonate to the solid acid is in the range of 1:10–10:1, and the weight of at least one selected from the group consisting of boron oxide and metaboric acid is in a proportion of 0.5–40% to the total weight.

2. A pesticidal composition comprising a) a pesticidal active ingredient, b) a surface active agent, c) a carbonate, d) a solid acid and e) boron oxide, wherein at least one of the carbonate and the solid acid is water-soluble, the total content of the carbonate and the solid acid is in a proportion of 5–90% to the total weight, the weight ratio of the carbonate to the solid acid is in the range of 1:10–10:1, and the weight of the boron oxide is in a proportion of 0.5–40% to the total weight.

3. A pesticidal composition comprising a) a pesticidal active ingredient, b) a surface active agent, c) a carbonate, d) a solid acid and e) metaboric acid, wherein at least one of the carbonate and the solid acid is water-soluble, the total content of the carbonate and the solid acid is in a proportion of 5–90% to the total weight, the weight ratio of the carbonate to the solid acid is in the range of 1:10–10:1, and the weight of the metaboric acid is in a proportion of 0.5–40% to the total weight.

4. A composition according to claim 1, wherein a) is in a proportion of 0.01–80% by weight and b) is in a proportion of 0.1–70% by weight to the total weight of the composition.

5. A composition according to claim 4, wherein the total weight of c) and d) is in a proportion of 10–70% by weight to the total weight.

6. A composition according to claim 2, wherein the weight ratio of c) to d) is in the range of 1:5–5:1.

7. A composition according to claim 2, wherein a) is in a proportion of 0.01–80% by weight and b) is in a proportion of 0.1–70% by weight to the total weight of the composition.

8. A composition according to claim 3, wherein a) is in a proportion of 0.01–80% by weight and b) is in a proportion of 0.1–70% by weight to the total weight of the composition.

9. A composition according to claim 7, wherein the total weight of c) and d) is in a proportion of 10–70% by weight to the total weight.

10. A composition according to claim 8, wherein the total weight of c) and d) is in a proportion of 10–70% by weight to the total weight.

* * * * *

UNITED STATES PATENT AND TRADEMARK OFFICE
CERTIFICATE OF CORRECTION

PATENT NO. : 5,232,701

DATED : August 3, 1993

INVENTOR(S) : Masao OGAWA et al

It is certified that error appears in the above-identified patent and that said Letters Patent is hereby corrected as shown below:

Column 21,

Claim 1, line 7, "5-9%" should read --5-90%--.

Signed and Sealed this

Seventeenth Day of May, 1994

Attest:

BRUCE LEHMAN

Attesting Officer    Commissioner of Patents and Trademarks